(12) United States Patent
Duffy (10) Patent No.: US 8,007,469 B2
(45) Date of Patent: Aug. 30, 2011

(54) MEDICAL INSTRUMENT INSERTER

(75) Inventor: Niall Duffy, Tuam (IE)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/182,659

(22) Filed: Jul. 30, 2008

(65) Prior Publication Data
US 2010/0030154 A1 Feb. 4, 2010

(51) Int. Cl.
*A61M 5/178* (2006.01)
(52) U.S. Cl. ........... 604/161; 604/3; 604/87; 604/148; 604/164.01; 604/164.06; 604/164.12; 604/200; 604/306; 604/159; 606/30; 606/37; 606/39; 606/41; 606/45; 606/46; 606/80; 606/82; 606/138; 606/159; 606/166; 606/167; 606/168; 606/170; 606/174; 606/182
(58) Field of Classification Search ........... 604/3, 87, 604/148, 164.01, 164.06, 164.12, 200, 306, 604/159; 606/30, 37, 39, 41, 45, 46, 80, 606/82, 138, 159, 166, 167, 168, 170, 174, 606/182
See application file for complete search history.

(56) References Cited

U.S. PATENT DOCUMENTS

| | | | |
|---|---|---|---|
| 2,018,149 A | | 10/1935 | Randle et al. |
| 2,256,942 A | | 9/1941 | Duffy |
| 3,624,901 A | * | 12/1971 | Pettit et al. ............... 30/90.4 |
| 3,898,733 A | | 8/1975 | Cormier |
| 4,394,828 A | | 7/1983 | Garbis et al. |
| 4,411,654 A | * | 10/1983 | Boarini et al. ........... 604/165.04 |
| 4,449,973 A | * | 5/1984 | Luther ..................... 604/161 |
| 4,596,559 A | * | 6/1986 | Fleischhacker ........ 604/164.05 |
| 4,631,059 A | * | 12/1986 | Wolvek et al. ............... 604/528 |
| 4,687,469 A | * | 8/1987 | Osypka ..................... 604/161 |
| 4,966,588 A | | 10/1990 | Rayman et al. |
| 4,985,018 A | * | 1/1991 | Smith ....................... 604/161 |
| 4,994,067 A | | 2/1991 | Summers |
| 4,997,424 A | * | 3/1991 | Little ....................... 604/161 |
| 5,125,904 A | | 6/1992 | Lee |
| 5,188,606 A | * | 2/1993 | Maloney et al. ........... 604/161 |
| 5,195,978 A | * | 3/1993 | Schiffer ..................... 604/161 |
| 5,250,033 A | * | 10/1993 | Evans et al. ............... 604/160 |

(Continued)

FOREIGN PATENT DOCUMENTS
WO WO 01/02047 A1 1/2001
(Continued)

OTHER PUBLICATIONS (PCT/US2009/050793) PCT Notification of Transmittal of the International Search Report and the Written Opinion of the International Searching Authority, Oct. 29, 2009.

(Continued)

*Primary Examiner* — Nicholas D Lucchesi
*Assistant Examiner* — Scott Medway (57) ABSTRACT

A catheter system for positioning an instrument within a body that includes a hub defining a lumen therethrough for passage of the instrument toward the body. The catheter system also includes an elongate tubular member defining a lumen therethrough. The lumen of the elongate tubular member is in communication with the lumen of the hub for further passage of the instrument toward the body. The system also includes a slitter member that is coupled to the hub. The slitter member is disposed to slit the elongate tubular member as the elongate tubular member moves relative to the hub.

25 Claims, 9 Drawing Sheets

U.S. PATENT DOCUMENTS

| | | | | |
|---|---|---|---|---|
| 5,330,460 A | * | 7/1994 | Moss et al. | 30/90.4 |
| 5,359,690 A | * | 10/1994 | Kaizu et al. | 385/134 |
| 5,397,333 A | * | 3/1995 | Knoepfler | 606/170 |
| 5,409,469 A | | 4/1995 | Schaerf | |
| 5,433,725 A | | 7/1995 | Christian et al. | |
| 5,586,990 A | | 12/1996 | Hahnen et al. | |
| 5,601,601 A | | 2/1997 | Tal et al. | |
| 5,651,781 A | | 7/1997 | Grace | |
| 5,665,100 A | | 9/1997 | Yoon | |
| 5,687,727 A | | 11/1997 | Kraus et al. | |
| 5,868,785 A | | 2/1999 | Tal et al. | |
| 5,873,854 A | * | 2/1999 | Wolvek | 604/104 |
| 5,873,858 A | * | 2/1999 | Schafer et al. | 604/161 |
| 5,922,001 A | | 7/1999 | Yoon | |
| 5,984,938 A | | 11/1999 | Yoon | |
| 5,984,939 A | | 11/1999 | Yoon | |
| 6,080,141 A | * | 6/2000 | Castro et al. | 604/523 |
| 6,148,521 A | * | 11/2000 | Eslambolchi et al. | 30/90.4 |
| 6,159,198 A | * | 12/2000 | Gardeski et al. | 604/523 |
| 6,247,235 B1 | | 6/2001 | Lawler | |
| 6,280,433 B1 | | 8/2001 | McIvor et al. | |
| 6,334,253 B1 | | 1/2002 | Cheng | |
| 6,368,337 B1 | | 4/2002 | Kieturakis et al. | |
| 6,497,681 B1 | * | 12/2002 | Brenner | 604/164.05 |
| 6,508,966 B1 | * | 1/2003 | Castro et al. | 264/138 |
| 6,544,247 B1 | | 4/2003 | Gardeski et al. | |
| 6,582,390 B1 | * | 6/2003 | Sanderson | 604/19 |
| 6,832,536 B2 | * | 12/2004 | Dittmar | 83/184 |
| 6,966,896 B2 | * | 11/2005 | Kurth et al. | 604/167.06 |
| 7,029,460 B2 | * | 4/2006 | Gardeski et al. | 604/160 |
| 7,338,481 B2 | | 3/2008 | Gardeski et al. | |
| D576,279 S | | 9/2008 | Bullemer et al. | |
| D576,280 S | | 9/2008 | Bullemer et al. | |
| 7,422,571 B2 | * | 9/2008 | Schweikert et al. | 604/167.04 |
| 7,462,167 B2 | * | 12/2008 | Kratz et al. | 604/164.05 |
| D608,003 S | | 1/2010 | Bullemer et al. | |
| D608,445 S | | 1/2010 | Bullemer et al. | |
| 2001/0044624 A1 | * | 11/2001 | Seraj et al. | 606/41 |
| 2002/0138041 A1 | * | 9/2002 | Zhang et al. | 604/164.01 |
| 2003/0050638 A1 | | 3/2003 | Yachia et al. | |
| 2003/0050639 A1 | | 3/2003 | Yachia et al. | |
| 2003/0095763 A1 | * | 5/2003 | Dallas et al. | 385/109 |
| 2003/0158565 A1 | | 8/2003 | Gardeski et al. | |
| 2003/0181935 A1 | | 9/2003 | Gardeski et al. | |
| 2004/0059348 A1 | | 3/2004 | Geske et al. | |
| 2005/0182435 A1 | | 8/2005 | Andrews et al. | |
| 2005/0256450 A1 | | 11/2005 | Palasis et al. | |
| 2005/0288551 A1 | * | 12/2005 | Callister et al. | 600/115 |
| 2006/0167417 A1 | | 7/2006 | Kratz et al. | |
| 2006/0235431 A1 | | 10/2006 | Goode et al. | |
| 2006/0247497 A1 | * | 11/2006 | Gardner | 600/188 |
| 2007/0079511 A1 | | 4/2007 | Osypka | |
| 2007/0175049 A1 | | 8/2007 | Goode et al. | |
| 2008/0033456 A1 | | 2/2008 | Catanese, III et al. | |
| 2008/0039833 A1 | | 2/2008 | Catanese, III et al. | |
| 2008/0108972 A1 | | 5/2008 | Andrews et al. | |
| 2008/0319524 A1 | | 12/2008 | Yachia et al. | |
| 2009/0049698 A1 | | 2/2009 | Drake et al. | |
| 2009/0054840 A1 | | 2/2009 | Drake et al. | |
| 2009/0071012 A1 | | 3/2009 | Shan et al. | |
| 2010/0030161 A1 | | 2/2010 | Duffy | |
| 2011/0000089 A1 | | 1/2011 | Goode et al. | |

FOREIGN PATENT DOCUMENTS

| | | |
|---|---|---|
| WO | WO 2007/089985 A1 | 8/2007 |
| WO | WO 2009/029558 A2 | 3/2009 |
| WO | WO 2009/029573 A1 | 3/2009 |
| WO | WO 2009/029558 A3 | 9/2009 |

OTHER PUBLICATIONS

Medtronic Technical Manual for the 6218RED Guide Catheter Slitter, 2002, 16 pgs.

* cited by examiner

MEDICAL INSTRUMENT INSERTER

FIELD

The present disclosure relates generally to medical devices and, more specifically, to a break away tab integrated slitter for removing a catheter, such as an introducer sheath, or other elongate tubular member used to move an elongate medical instrument at a desired position within a body.

BACKGROUND

The statements in this section merely provide background information related to the present disclosure and may not constitute prior art.

Various devices have been proposed for introducing and/or positioning elongate medical instruments in the human body. For instance, various catheter systems, introducer sheaths, and other elongate tubular members have been proposed for these purposes. More specifically, these devices include a proximal portion that remains outside the body and a tubular portion that extends into the body. A lumen extends through the proximal portion and the tubular portion. A medical instrument, such as a cardiac pacemaker lead or other vascular instrument, passes through the lumen into the body, and then the medical professional positions the medical instrument into a desired position. For instance, in some embodiments, the medical instrument is positioned within the patient's heart, blood vessel, or other portion of the body. Then, the medical professional removes the tubular portion of the catheter system.

Many catheter systems have been proposed that are designed to be removed without disturbing (i.e., inadvertently moving) the medical instrument from its desired position. For instance, some catheter systems include an elongate tubular member that can be torn and peeled apart longitudinally while being pulled out of the body. Other systems rely on an independent slitter with a blade that slits the elongate tubular member as it is pulled out of the body.

SUMMARY

A catheter system for positioning an instrument within a body is disclosed that includes a hub defining a lumen therethrough for passage of the instrument toward the body. The catheter system also includes an elongate tubular member defining a lumen therethrough. The lumen of the elongate tubular member is in communication with the lumen of the hub for further passage of the instrument toward the body. The system also includes a slitter member that is coupled to the hub. The slitter member is disposed to slit the elongate tubular member as the elongate tubular member moves relative to the hub.

In still another aspect, a method is disclosed for operating a catheter system that includes a hub, an elongate tubular member, a slitter member coupled to the hub, and a moveable member that is removeably coupled to the hub via a break-away tab. The method includes breaking the break-away tab and moving the moveable member relative to the hub to thereby advance the elongate tubular member toward the slitter member. The method also includes slitting the elongate tubular member with the slitter member as the moveable member is moved relative to the hub.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 1:
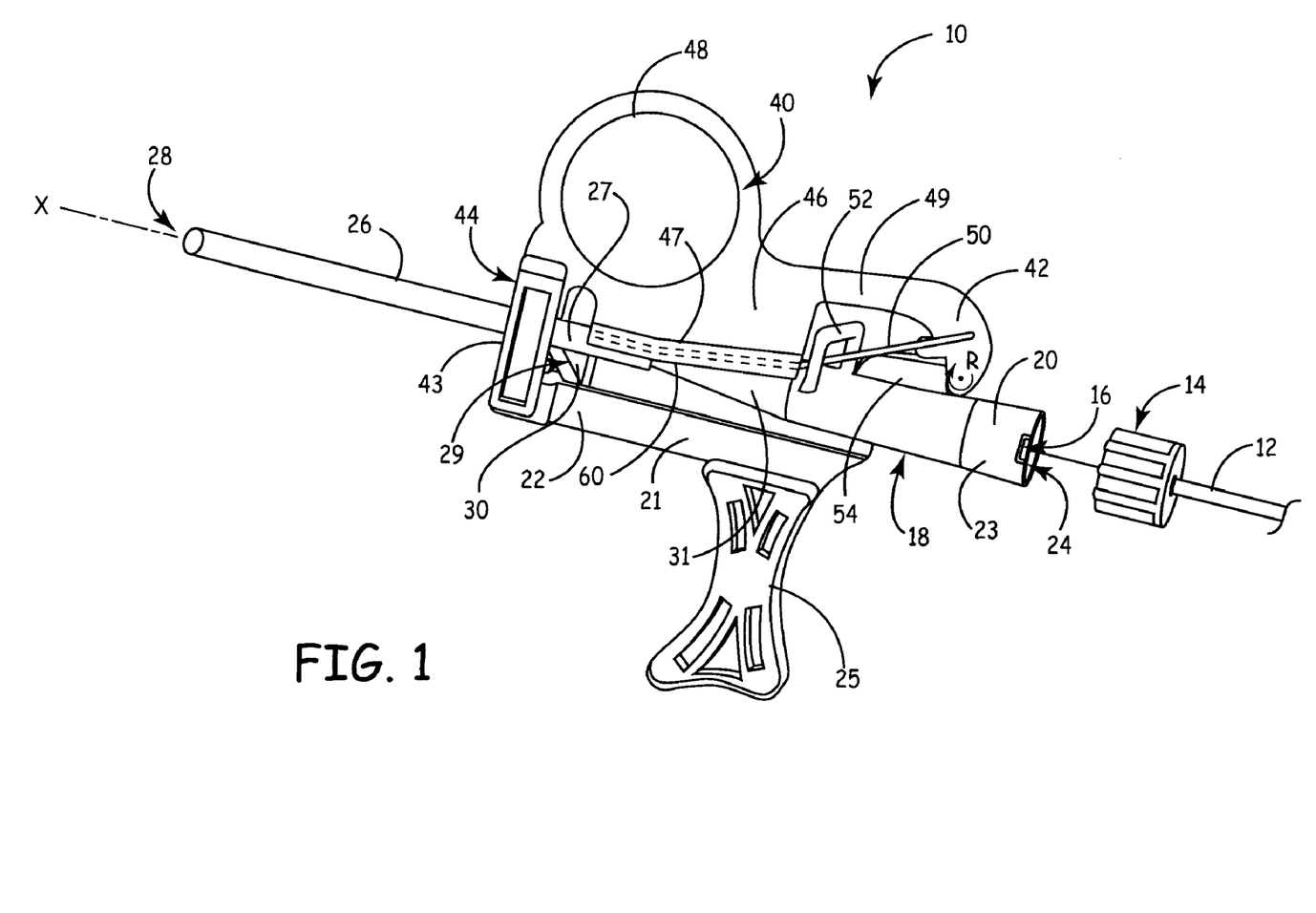
FIG. 1 is a perspective view of a catheter system according to various teachings of the present disclosure.
Figure 2:
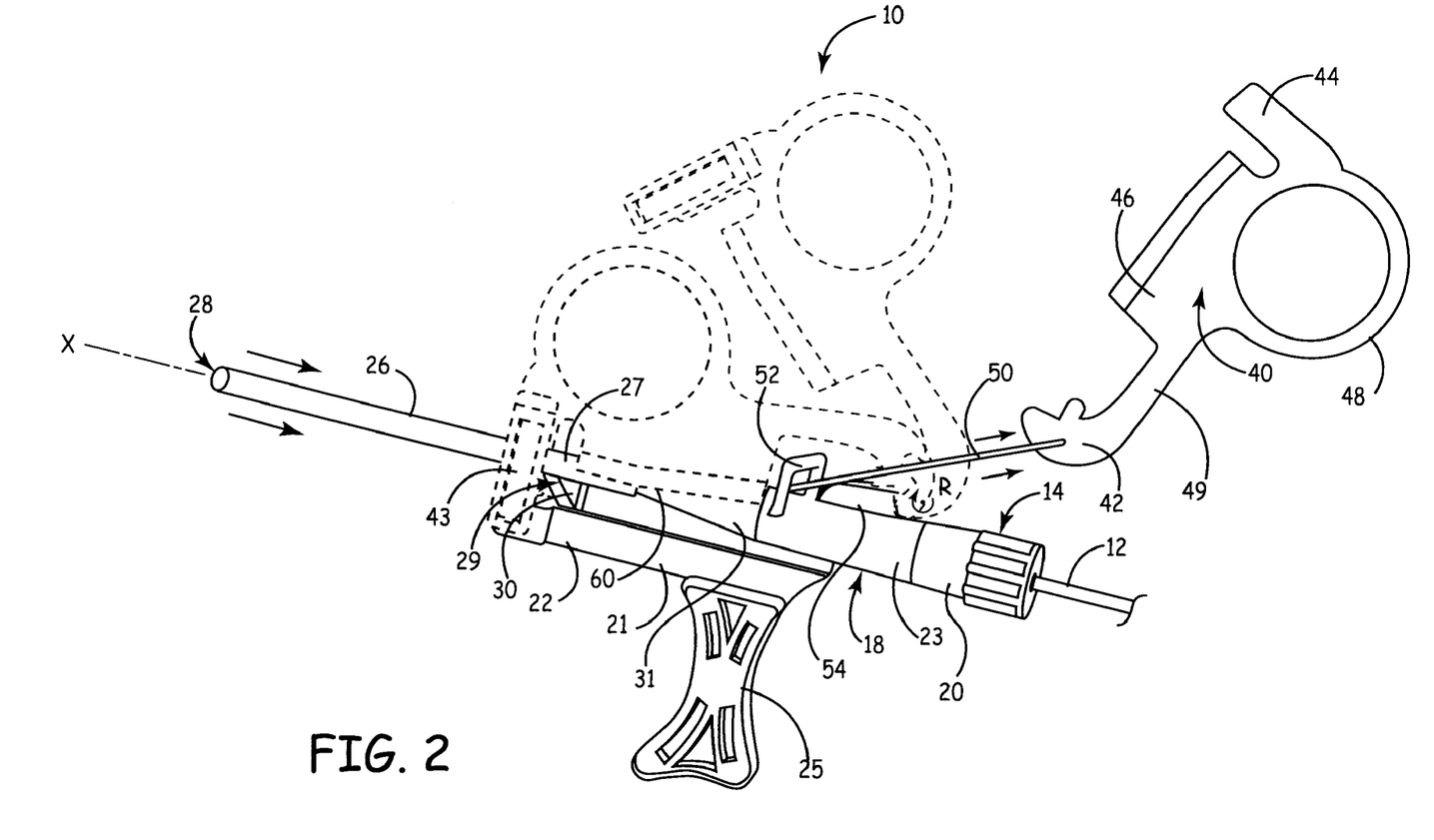
FIG. 2 is a perspective view of the catheter system of FIG. 1 shown in a slitting configuration.

Referring initially to FIGS. 1 and 2, a catheter system 10 is illustrated. The catheter system 10 is operable for positioning a medical instrument 12, such as a cardiac pacemaker lead, vascular instrument, a suture sleeve, or other elongate medical instrument, within a body of a patient. It will be appreciated that, although the following discussion will be related to positioning a cardiac pacemaker or other vascular instrument, the catheter system 10 can be used for positioning any suitable medical instrument 12 without departing from the scope of the present disclosure.

In the embodiments illustrated, the catheter system 10 generally includes an engagement member 16 for removably attaching the catheter system 10 and the medical instrument 12. In some embodiments, the engagement member 16 couples to a standard valve 14 to achieve a removable luer-type coupling. The medical instrument 12 passes through the valve 14 and through the catheter system 10 as will be described in greater detail.

The system 10 also includes a hub 18 (FIGS. 1-3) that defines a proximal end 20 and a distal end 22. The hub 18 also defines a base 21, which can have a solid, rectangular cross section, and a lumen portion 23, which can be hollow and tubular. The lumen portion 23 defines a lumen 24 therethrough. The lumen 24 defines a longitudinal axis X. In some embodiments, an outer surface 31 of the lumen portion 23 and the lumen 24 is tapered along the longitudinal axis X.

Figure 3:
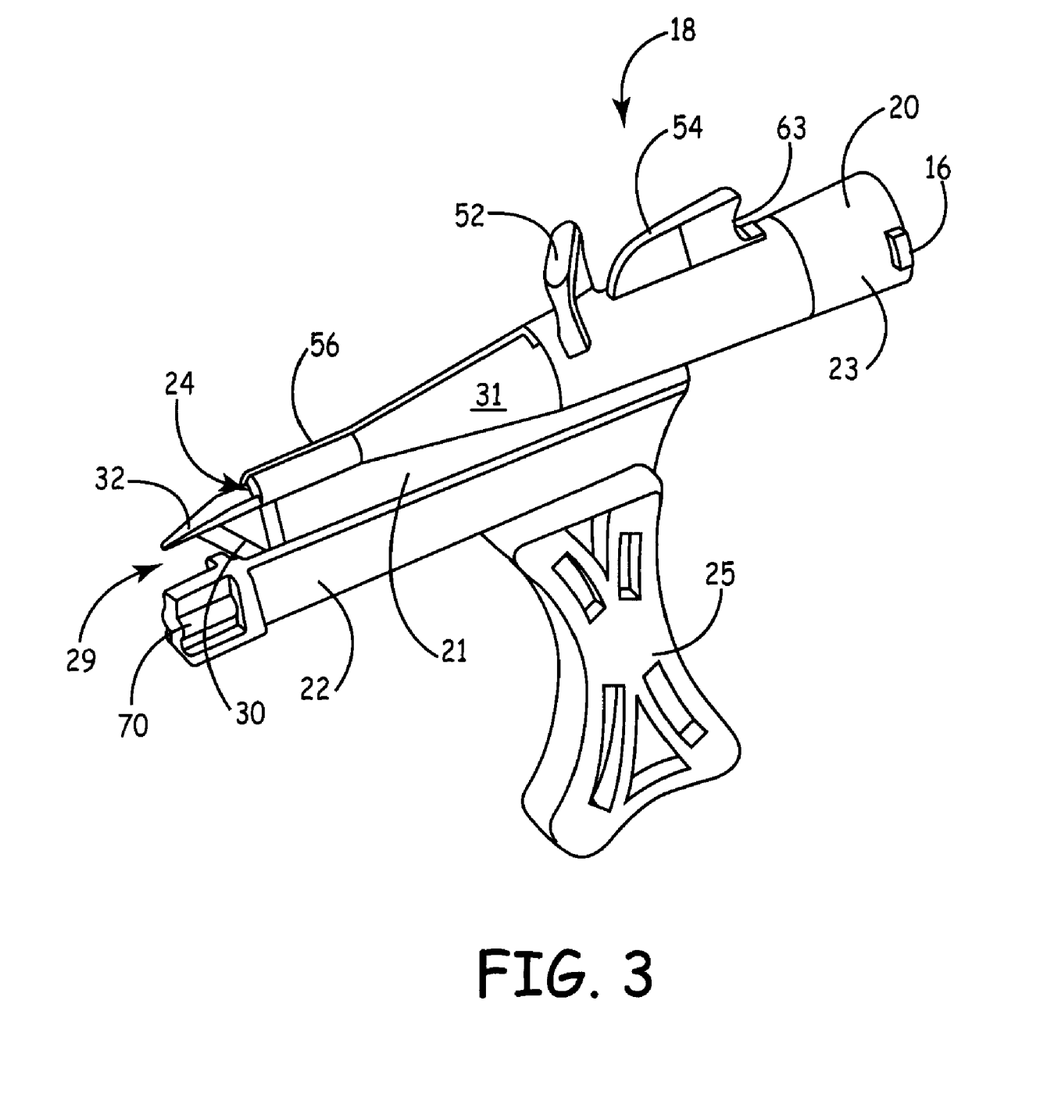
FIG. 3 is a perspective view of a hub of the catheter system of FIG. 1.

The hub 18 can also include a grip member 25 for holding the hub 18. In some embodiments, the grip member 25 extends transversely away from the longitudinal axis X. In some embodiments, the grip member 25 is integrally attached to the base 21 such that the grip member 25 and the base 21 are monolithic. Moreover, in some embodiments, the grip member 25 and base 21 are made out of a molded, polymeric material, such as nylon, HDPE, polycarbonate, PU, ABS, composite materials, polymer blends such as rubber toughened nylon, nylon co-polymers such as Pebax, or filled materials such as talc filled polypropylene.

As shown, the system 10 further includes an elongate tubular member 26. The elongate tubular member 26 is hollow so as to define a lumen 28 extending therethrough. A proximal end 27 of the tubular member 26 is coupled to the distal end 22 of the hub 18 such that the lumen 28 of the tubular member 26 is in communication with the lumen 24 of the hub 18. In some embodiments, the tubular member 26 is made out of a flexible, polymeric material, such as Pebax, Nylon, PE, multi-layered extrusions, or braided layered assemblies such as a Pebax/braid/PTFE liner & variable longitudinal durometer tube assemblies.

As will be described in greater detail below, the medical instrument 12 can pass through the proximal end 20 of the hub 18, through the lumen 24, and pass further into the lumen 28 of the tubular member 26 to be positioned within the heart, blood vessel, or other desired portion of the human body. Once the medical instrument 12 is properly positioned, the tubular member 26 can be slit and removed from the body without disturbing or otherwise moving the medical instrument 12 from its desired position as will be discussed.

Figure 5:
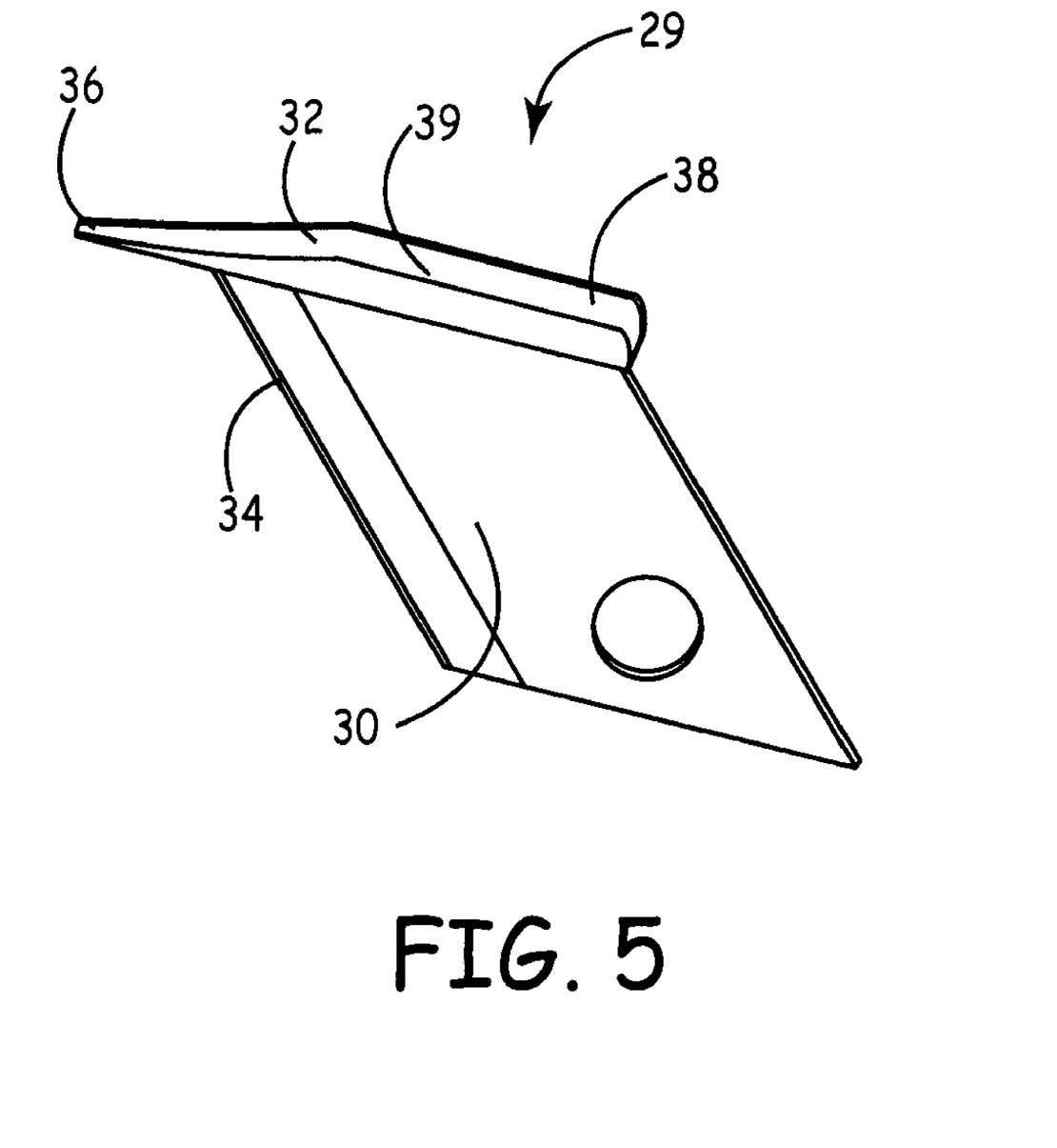
FIG. 5 is a perspective view of a slitter member of the catheter system of FIG. 1.

Furthermore, the system 10 includes a slitter member 29 (FIGS. 1, 2, and 5). The slitter member 29 can include a blade 30 and a spade 32. As shown in FIG. 5, the blade 30 includes a sharpened leading edge 34. The spade 32 is fixedly attached to the blade 30. In some embodiments, the blade 30 and spade 32 are made out of electro-polished stainless steel and are laser welded together; however, it will be appreciated that the blade 30 and spade 32 can be made out of any suitable material and can be attached in any suitable manner without departing from the scope of the present disclosure. Also, it will be appreciated that the blade 30 and spade 32 can be separate from each other within the catheter system 10 without departing from the scope of the present disclosure.

The spade 32 can include a leading portion 36 and a rear portion 38. In some embodiments, the leading portion 36 is pointed and the spade 32 widens toward the rear portion 38 (i.e., the rear portion 38 is wider than the leading portion 36). The spade 32 is attached to the blade 30 such that the leading portion 36 is spaced forward from the leading edge 34 of the blade. Also, in some embodiments, a top surface 39 of the spade 32 is curved outward from the blade 30.

The slitter member 29 can be fixedly attached to the hub 18. As shown in FIGS. 1 and 2, the slitter member 29 can be fixed adjacent the distal end 22 of the hub 18 immediately forward of the lumen 24 of the hub 18. In some embodiments, the curved top surface 39 of the spade 32 is continuous with respect to the end of the lumen 24 of the hub 18. Also, the slitter member 29 can be attached such that the leading edge 34 of the blade 30 is disposed at a positive, acute angle with respect to the longitudinal axis X. In other words, the portion of the leading edge 34 adjacent the spade 34 is forward of the other portions of the leading edge 34. It will be appreciated that once the slitter member 29 is attached to the hub 18, the slitter member 29 and hub 18 are a single unit, which makes slitting of the tubular member 26 simple and ergonomic as will be discussed in greater detail below.

Figure 4:
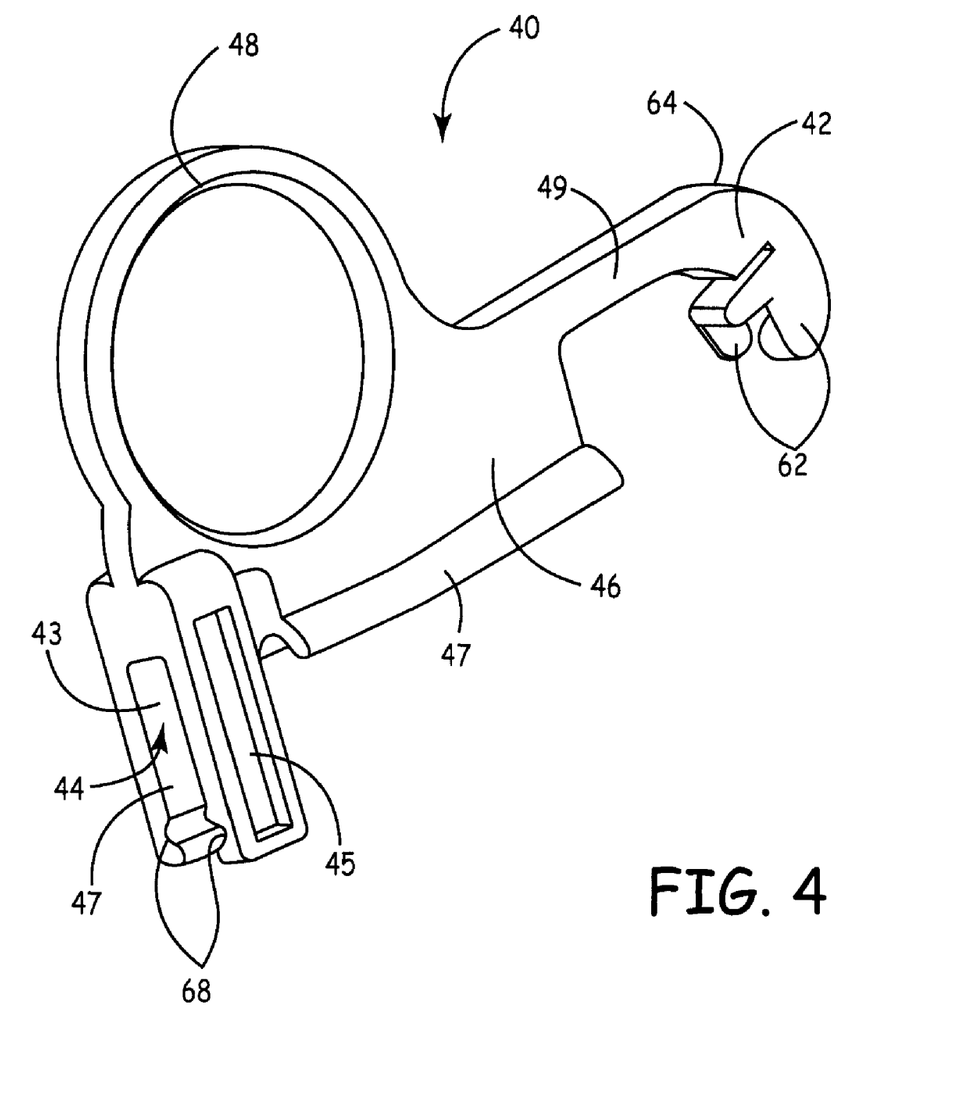
FIG. 4 is a perspective view of a moveable member of the catheter system of FIG. 1.

Moreover, as shown in FIGS. 1, 2, and 4, the system 10 includes a moveable member 40 that is moveably coupled to the hub 18 and that is coupled to the elongate tubular member 26 in a manner to be discussed below. As will be discussed, the moveable member 40 is operable to advance the elongate tubular member 26 toward the slitter member 29 as the moveable member 40 is moved relative to the hub 18. As such, the slitter member 29 slits the elongate tubular member 26.

In some embodiments, the moveable member 40 includes a first coupling member 42 that rotationally and removably couples the moveable member 40 to the lumen portion 23 of the hub 18. More specifically, the first coupling member 42 is rotationally and removably coupled adjacent to the proximal end 20 of the hub 18 on a side of the longitudinal axis X opposite from the grip member 25. As will be described in greater detail, the moveable member 40 rotates about an axis R due to the first coupling member 42, and the moveable member 40 also detaches from the hub 18 to move away from the axis R.

Also, in some embodiments, the moveable member 40 includes a second coupling member 44 that removably couples the moveable member 40 adjacent the distal end 22 of the base 21 of the hub 18. In some embodiments, the second coupling member 44 is a coupling fork 43 with a first arm 45 and a second arm 47 (FIG. 4). The first arm 45 and second arm 47 removably couple to opposing sides the hub 18 in a manner to be discussed in greater detail below.

Additionally, the arms 45, 47 of the coupling fork 43 can each include a grooved portion 68 (FIG. 4), and the hub 18 can include corresponding protrusions 70 (FIG. 3). The grooved portions 68 receive the corresponding protrusion 70 to removably couple the coupling fork 43 and the hub 18. It will be appreciated that the hub 18 could include the grooved portions 68, and the fork 43 could include the corresponding protrusions 70 without departing from the scope of the present disclosure.

The moveable member 40 also includes a central portion 46 that is generally disposed between the first coupling member 42 and second coupling member 44. The central portion 46 is generally thin and elongate. Also, the central portion 46 can include curved flanges 47 that extend transversely from opposite sides of the central portion 46. The flanges 47 are curved outward from the central portion 46 to substantially mate with the outer surface 31 of the hub 18. In some embodiments, the longitudinal taper of the outer surface 31 substantially matches the longitudinal taper of the flanges 47 such that the flanges 47 mate and conform to the outer surface 31.

Furthermore, the moveable member 40 can include a handle portion 48. In some embodiments, the handle portion 48 can be ring-shaped; however, it will be appreciated that the handle portion 48 can be partially ring-shaped, the handle portion 48 can be axially straight and extend transversely from the longitudinal axis X, or the handle portion 48 can have any other suitable shape. As shown in FIG. 1, the handle portion 48 is disposed generally between the first and second coupling members 42, 44.

The central portion 46 of the moveable member 40 also includes a lever portion 49. The lever portion 49 is generally straight along its axis. The lever portion 49 extends between the handle portion 48 and the first coupling member 42.

In some embodiments, the first and second coupling members 42, 44, the handle portion 48, and the lever portion 49 are each integrally attached such that the moveable member 40 is monolithic. Also, in some embodiments, the moveable member 40 is made out of a molded polymeric material, such as nylon, HDPE, polycarbonate, PU, ABS, composite materials, polymer blends such as rubber toughened nylon, nylon co-polymers such as Pebax, or filled materials such as talc filled polypropylene.

Additionally, the catheter system 10 can include a tube coupling member 50. The tube coupling member 50 can be an elongate, flat braided shaft. The tube coupling member 50 is fixedly attached to the proximal end 27 of the tubular member 26. In some embodiments, the tube coupling member 50 is separately attached to the tubular member 26 via an adhesive, via an overmolding process, or by welding. Also, in some embodiments, the tube coupling member 50 is integrally attached to the tubular member 26 such that the tubular member 26 and the tube coupling member 50 are monolithic. Moreover, in some embodiments, the tube coupling member 50 is partially curved to substantially wrap around the outside of the spade 32 on both sides of the blade 30. Further rearward, the tube coupling member 50 becomes thinner and more flat and lies atop the outer surface 31 of the hub 18. In some embodiments, the tube coupling member 50 is sealed to the hub 18 to keep contaminants out of the lumen 24 as will be discussed in greater detail below.

The tube coupling member 50 generally couples the proximal end 27 of the tubular member 26 and the lever portion 49 of the moveable member 40. In some embodiments, the tube coupling member 50 is coupled to the moveable member 40 between the handle portion 48 and the first coupling member 42, immediately adjacent the first coupling member 42. Also, in some embodiments, the tube coupling member 50 extends into an opening 51 of the lever portion 49 and is attached thereto using an adhesive, such as cyanoacrylate. The tube coupling member 50 can also be attached to the moveable member 40 via overmolding or by a mechanical grip fit. However, it will be appreciated that the tube coupling member 50 can be coupled in any suitable manner without departing from the scope of the present disclosure.

Thus, referring initially to FIG. 1, the operation of the catheter system 10 will be discussed. The valve 14 is attached to the hub 18. Then, the tubular member 26 is inserted into the body (not shown) through a prepared incision (not shown). Next, the medical instrument 12 is inserted by passing through the lumen 24 and further passing through the lumen 28 into the body. The valve 14 can be configured to inhibit backflow of bodily fluids and to facilitate positioning of the instrument 12 within the body and/or dye injection. Also, once the instrument 12 is in the desired position within the body, the valve 14 can be tightened to maintain the position of the instrument 12.

Then, the user grasps the grip member 25 with one hand and the handle portion 48 with the other hand. To begin slitting the tubular member 26, the user begins pulling and rotating the moveable member 40 and away from the axis X, thereby pivoting the moveable member 40 relative to the hub 18 about the axis R. This movement advances the tubular member 26 toward the slitter member 29, and the blade 30 begins forming a slit longitudinally in the tubular member 26. Also, because the handle portion 48 is spaced from the first coupling member 42 by the axial length of the lever portion 49, the lever portion 49 acts as a lever arm and provides a mechanical advantage for slitting the tubular member 26. It will be appreciated that this mechanical advantage can greatly facilitate slitting the tubular member 26, especially in the proximal end 27 of the tubular member 26.

Also, because of the shape of the spade 32 and the relative position between the spade 32 and blade 30 (described in detail above), the leading portion 36 of the spade 32 guides the elongate tubular member 26 toward the leading edge 34 of the blade 30. Accordingly, the slitter member 29 creates a uniform slit longitudinally in the tubular member 26, the tubular member 26 is unlikely to twist about its axis, and the medical instrument 12 is less likely to be moved during slitting.

Also, the taper of the outer surface 31 of the hub 18 separates the tubular member 26 about the slit and guides the slit portion of the tubular member 26 toward the proximal end 20 of the hub 18. As such, the tubular member 26 is unlikely to twist about its axis, and the medical instrument 12 is less likely to move during slitting.

Once the moveable member 40 has been rotated to its apex about the first coupling member 42, the user pulls the moveable member 40 further away from the hub 18 and detaches the first coupling member 42 from the hub 18 (FIG. 2). Moreover, in some embodiments, the moveable member 40 includes a rounded back surface 64 (FIGS. 1, 2, and 4) located adjacent the first coupling member 42 on a side opposite the fin 54. Once the moveable member 40 begins to detach from the hub 18, the rounded back surface 64 can continue to rotationally support the moveable member 40 on the hub 18. In other words, the moveable member 40 rotates on the hub 18 via the rounded back surface 64.

Then the user pulls the moveable member 40 generally along the axis X away from the hub 18 and slits the remaining portion of the tubular member 26 as it is pulled from the body. It will be appreciated that the handle portion 48 creates a pulling force on the tubular member 26, and the grip member 25 creates an opposing force to keep the hub 18 generally stationary with respect to the body during this step. Thus, the medical instrument 12 is less likely to move during slitting.

In some embodiments, the hub 18 further includes a guide loop 52 that at least partially encompasses the elongate tubular member 26. In the embodiments illustrated, the guide loop 52 is disposed adjacent the proximal end 20 of the hub 18, forward from first coupling member 42. In some embodiments, the guide loop 52 is integrally attached with the other portions of the hub 18 to be monolithic with the hub; however, the guide loop 52 can be removably attached to the hub 18. It will be appreciated that the guide loop 52 retains and guides the slit tubular member 26 generally along the axis X as the moveable member 40 moves relative to the hub 18. Accordingly, the tubular member 26 is less likely to twist along the axis X, and the medical instrument 12 is less likely to move during slitting.

Moreover, in some embodiments, the hub 18 further includes a guide fin 54 that extends transversely away from the axis X adjacent the proximal end 20 of the hub 18, between the guide loop 52 and the first coupling member 42. In some embodiments, the guide fin 54 is integrally attached to remaining portions of the hub 18 so as to be monolithic with the hub 18; however, the guide fin 54 can be removably coupled to the hub 18 as well. It will be appreciated that, as the tubular member 26 is pulled along the hub 18, the guide fin 54 extends into the slit formed in the tubular member 26 and generally inhibits rotation (i.e., twisting) of the tubular member 26 about the axis X. Accordingly, the medical instrument 12 is less likely to be inadvertently moved during slitting.

Also, in some embodiments, the hub 18 includes a recess 63 (FIG. 3) for coupling the first coupling member 42 to the hub 18. In some embodiments, the recess 63 is included proximally on the fin 54, and the first coupling member 42 is substantially rounded so as to rotationally fit within the recess 63. Furthermore, in some embodiments, the first coupling member 42 can include side members 62 (see FIGS. 1, 2, and 4). In some embodiments, the side members 62 are thin flanges that extend over opposite sides of the fin 54. The side members 62 generally retain the moveable member 40 for pivoting about the axis R so as to retain the pivot axis R in a substantially perpendicular position relative to the hub 18. Because of the mating of the recess 63 and the first coupling member 42 and because of the side members 62, the tubular member 26 is more likely to be pulled substantially straight along the axis X, and the instrument 12 is more likely to remain in position during slitting.

Referring back to the method of operating the catheter system 10, the user finishes slitting and removing the tubular member 26 from the body. Subsequently, the valve 14 can be loosened, and the hub 18 can slide off from the medical instrument 12, leaving the medical instrument 12 in the desired position. In some embodiments, the hub 18 includes a longitudinal slot 56 (FIG. 3) adjacent the distal end 22 of the hub 18 on a side opposite to the grip member 25, and the slot 56 is in communication with the lumen 24 to facilitate sliding removal of the hub 18 from over the medical instrument 12. Then, the medical instrument 12 is ready for further medical procedures, such as attachment of a pacemaker.

Accordingly, the catheter system 10 allows for easy implantation (i.e., movement and positioning) of the medical instrument 12. The slitting of the tubular member 26 can be performed more easily because the lever action of the moveable member 40. Also, the system 10 can be performed by one person because of the various ergonomic features described above. Moreover, the system 10 includes several features that inhibits the tubular member 26 from twisting about its axis, thereby making it less likely to inadvertently move the tubular member 26 during slitting. In addition, manufacture of the catheter system 10 can be completed relatively quickly and less expensively than systems of the prior art.

Moreover, in some embodiments, the system 10 can include a seal 60 for sealing the tube coupling member 50 and/or the moveable member 40 to the hub 18. The seal 60 thereby reduces contamination of the lumen 24 of the hub 18 and the lumen 28 of the tubular member 26. In some embodiments, the seal 60 is a low strength adhesive, such as silicone; however, it will be appreciated that the seal 60 could be made out of any suitable material.

Specifically, in some embodiments, the seal 60 extends over the tube coupling member 50 and the outer surface 31 such that the slot 56 is substantially sealed. In other embodiments, one seal 60 extends over one of the flanges 47 and the outer surface 31, and another seal 60 extends over another of the flanges 47. In still other embodiments, the seal 60 is created by overmolding the tube coupling member 50 with the material of the hub 18. For instance, in the embodiment of FIG. 9, the seal 360 is created by overmolding the tube coupling member 50 with the material of the hub 18. It will be appreciated that the seal 60, 360 is of a generally low strength and/or generally does not adhere well to the hub 18 such that the seal 60, 360 breaks easily upon movement of the moveable member 40, 340 relative to the hub 18, 318. Accordingly, the system 10, 310 is more likely to remain sanitary due to the seal 60, 360.

Figure 6:
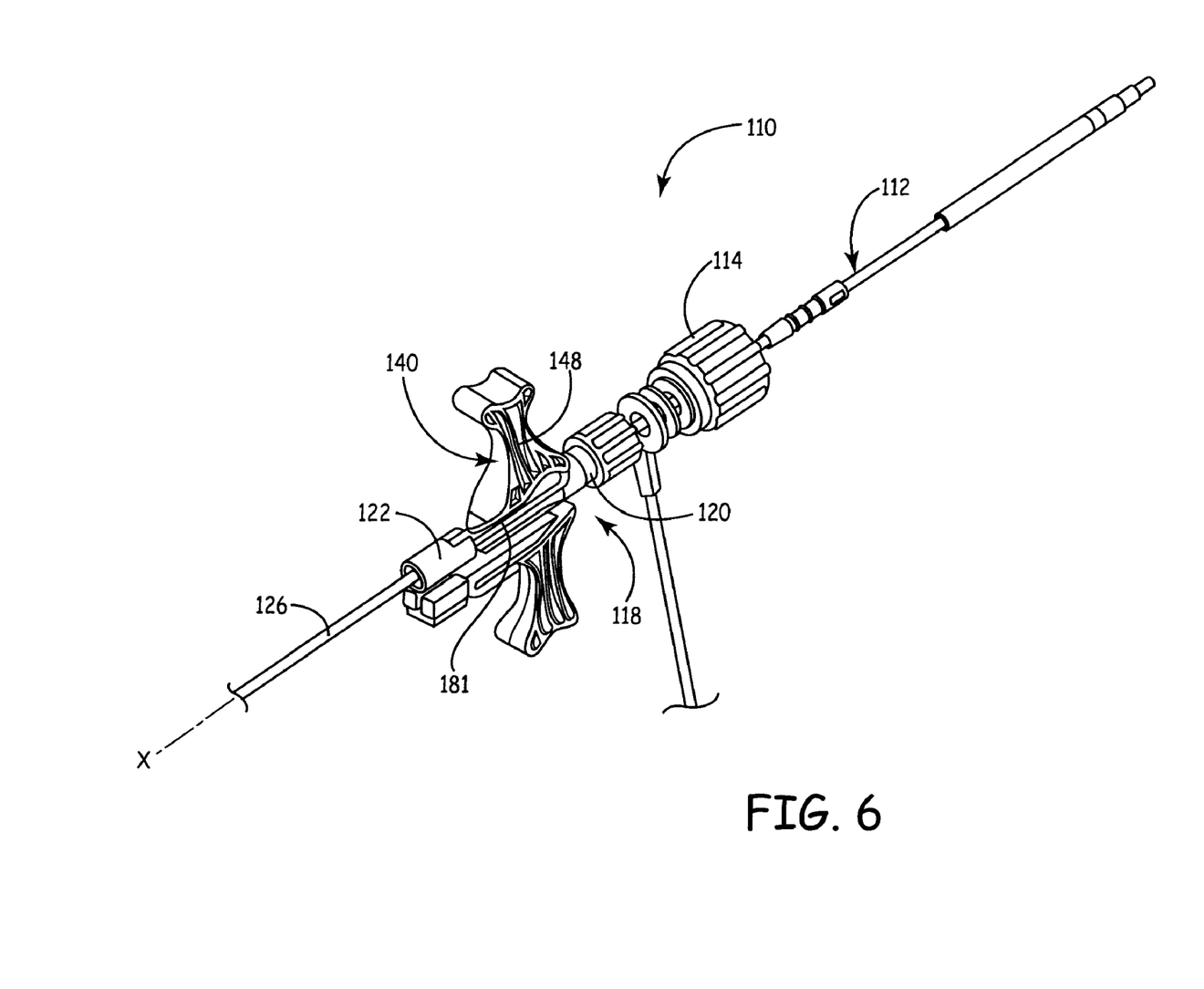
FIG. 6 is a perspective view of other embodiments of a catheter system according to the present disclosure.
Figure 7:
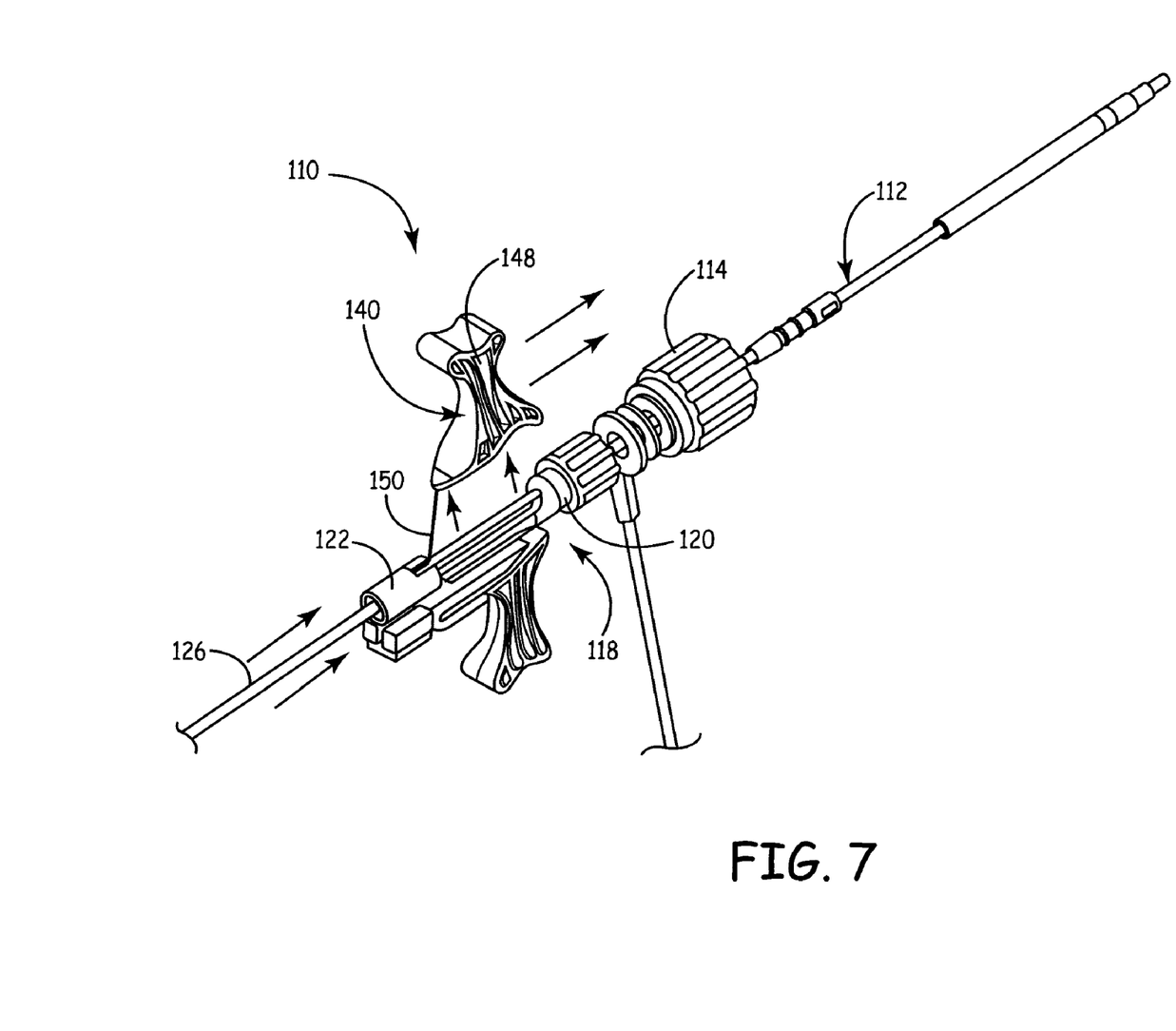
FIG. 7 is a perspective view of the catheter system of FIG. 6 shown in a slitting configuration.

Referring now to FIGS. 6 and 7, the catheter system 110 is illustrated according to various other embodiments of the present disclosure. It will be appreciated that components similar to those of the embodiment of FIGS. 1-5 are identified by similar reference numerals increased by 100.

In some embodiments, the catheter system 110 includes a moveable member 140 with a handle member 148 that extends generally transverse to the axis X. In some embodiments, the handle member 148 is substantially perpendicular to the axis X. The moveable member 140 is coupled to the hub 118 via a break-away tab 181 (FIG. 6). The break-away tab 181 can be formed to extend generally around the moveable member 140. The break-away tab 181 can be formed using a relatively low strength adhesive that couples the moveable member 140 and the hub 118. Also, the moveable member 140 and the hub 118 can be molded together to be monolithic, and the break-away tab 181 can be a thin section of molded material formed during this molding process.

The slitting procedure is somewhat similar to that discussed above. However, to begin slitting, the break-away tab 181 is first broken. In some embodiments, the break-away tab 181 is broken by pressing the moveable member 140 toward the axis X and toward the hub 118. In some embodiments, the break-away tab 181 is further broken by pivoting the moveable member 140 distally.

Once the break-away tab 181 has been broken, the moveable member 140 is pulled transversely away from the axis X and away from the hub 118. Because of the tube coupling member 150, this movement advances and slits the tubular member 126 similar to the embodiments of FIGS. 1-5. Next, the moveable member 140 is pulled generally along the axis X proximally away from the hub 118 to complete slitting of the tubular member 126. Finally, the hub 118 slides over the instrument 112 to complete the operation of the system 110.

In some embodiments, the distal end 122 of the hub 118 is removably coupled to other portions of the hub 118. Thus, in the final step of removing the hub 118, the proximal end 120 is removed from over the instrument 112, and then the distal end 122 is separately removed from the instrument 112.

Figure 8:
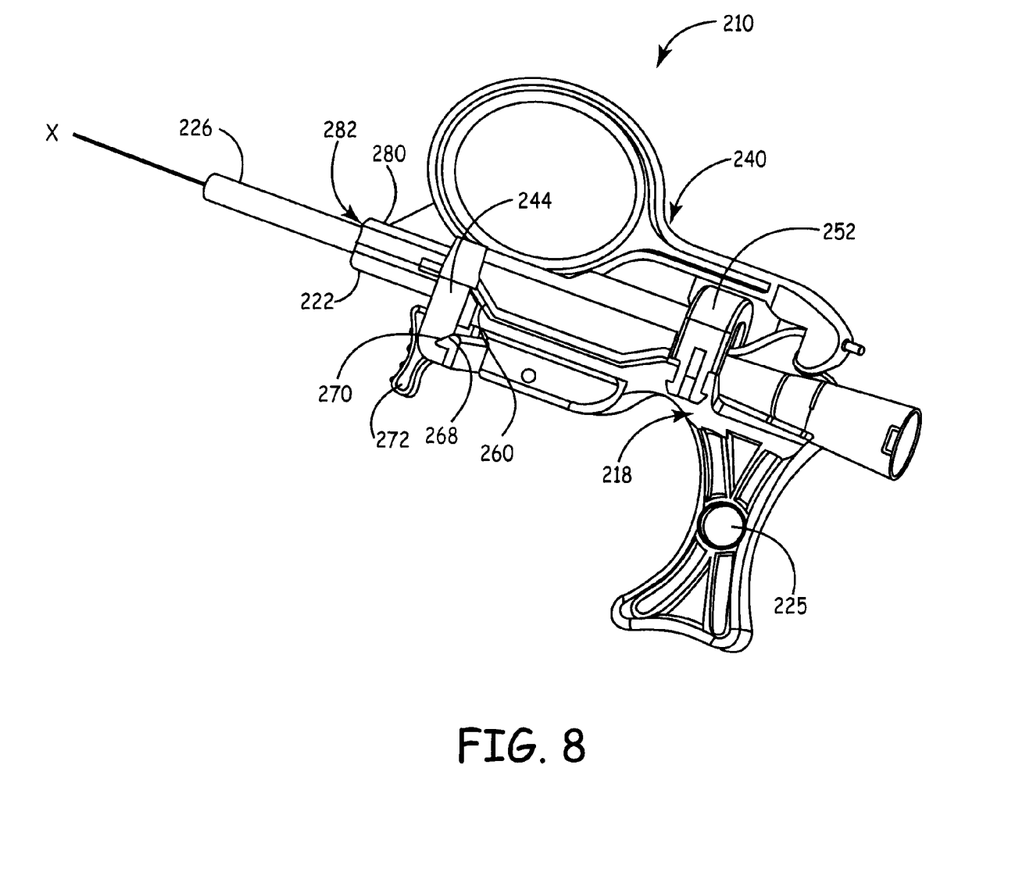
FIG. 8 is a perspective view of still other embodiments of a catheter system according to the present disclosure.

Referring now to FIG. 8, the catheter system 210 is illustrated according to various other embodiments of the present disclosure. It will be appreciated that components similar to those of the embodiment of FIGS. 1-5 are identified by similar reference numerals increased by 200.

As shown, the catheter system 210 can include a guide loop 252 that is removably attached to the hub 218. The guide loop 252 can be coupled via a snap fit. Accordingly, in some embodiments, by including a guide loop 252 that is removably attached, the manufacturability of the system 210 can be increased.

Also, the distal end 222 of the hub 218 and the distal end 280 of the moveable member 240 cooperate to define a rounded opening 282. The rounded opening 282 encompasses the tubular member 226 and can further seal the system 210 from contaminants.

Furthermore, the system 210 can include a trigger member 272 adjacent the distal end 222 of the hub 218 on a side opposite to the moveable member 240. The trigger member 272 extends generally transverse to the axis X. The trigger member 272 is resiliently flexible. Also, the second coupling member 244 removably couples to the trigger member 272. More specifically, when the user holds the grip member 225, the user can also resiliently squeeze the trigger member 272 toward the grip member 225 with the same hand. This movement causes the protrusions 270 to move out of the corresponding grooves 268 to detach the second coupling member 244 from the hub 218. Accordingly, the trigger member 272 provides a greater amount of control during slitting.

Figure 9:
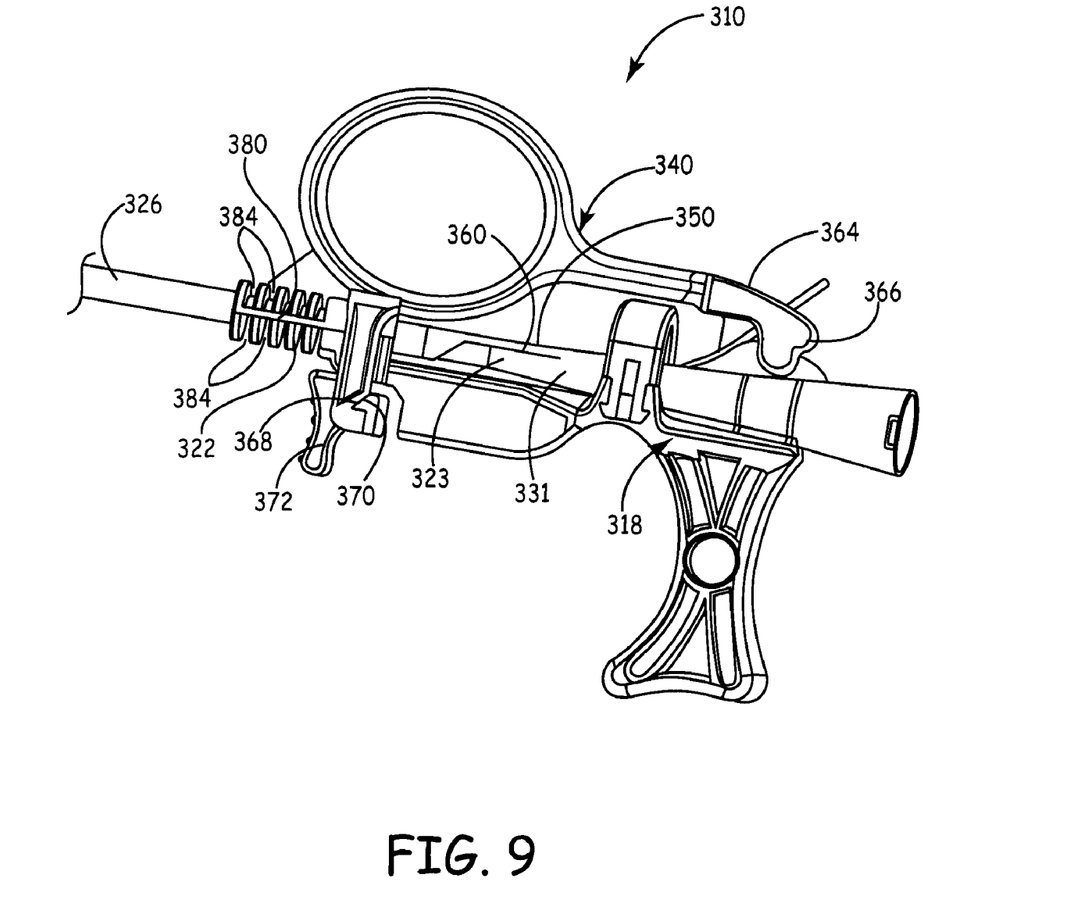
FIG. 9 is a perspective view of still other embodiments of a catheter system according to the present disclosure.

Referring now to FIG. 9, the catheter system 310 is illustrated according to various other embodiments of the present disclosure. It will be appreciated that like components similar to those of the embodiment of FIGS. 1-5 are identified by similar reference numerals increased by 300.

As shown, the rounded back surface 364 includes a camming feature 366 (FIG. 9). It will be appreciated that, as the moveable member 340 begins rotating on the back surface 364, the camming feature 366 cams the moveable member 340 up and away from the hub 18. Accordingly, the camming feature 366 ergonomically aids the user in pulling the moveable member 340 from the hub 318 for slitting purposes.

Furthermore, the system 310 includes reliefs 384 in the distal end 322 of the hub 318 and the distal end 380 of the moveable member 340. The reliefs 384 can increase the manufacturability of the system 310 and can increase the flexibility of the system 310 for greater control during slitting of the tubular member 326.

Certain terminology is used herein for purposes of reference only, and thus is not intended to be limiting. For example, terms such as "upper," "lower," "above," "below," "top," "upward," and "downward" refer to directions in the drawings to which reference is made. Terms such as "front," "back," "rear," and "side," describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first," "second," and other such numerical terms referring to structures do not imply a sequence or order unless clearly indicated by the context.

When introducing elements or features and the exemplary embodiments, the articles "a," "an," "the" and "said" are intended to mean that there are one or more of such elements or features. The terms "comprising," "including," and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

The description of the disclosure is merely exemplary in nature and, thus, variations that do not depart from the gist of the disclosure are intended to be within the scope of the disclosure. Such variations are not to be regarded as a departure from the spirit and scope of the disclosure.

What is claimed is:

1. A catheter system for positioning an instrument within a body, the catheter system comprising:
   a hub defining a lumen therethrough for passage of the instrument toward the body;
   an elongate tubular member defining a lumen therethrough, the lumen of the elongate tubular member being in communication with the lumen of the hub for further passage of the instrument toward the body;
   a slitter member that is coupled to the hub, the slitter member disposed to slit the elongate tubular member as the elongate tubular member moves relative to the hub; and
   a moveable member removably coupled to the hub and coupled to the elongate tubular member, wherein the moveable member is movable to advance the elongate tubular member toward the slitter member as the moveable member is moved relative to the hub such that the slitter member slits the elongate tubular member, and further wherein at least the movable member maintains the elongate tubular member in a fixed position relative to the hub prior to moving the movable member relative to the hub to advance the elongate tubular member.

2. The catheter system of claim 1, wherein the slitter member includes a blade and a spade, the spade including a leading portion that is spaced from a leading edge of the blade, the leading portion operable to guide the elongate tubular member toward the leading edge of the blade to be slit.

3. The catheter system of claim 2, wherein the blade and the spade are welded together.

4. The catheter system of claim 2, wherein the spade includes a rear portion, and wherein the rear portion includes a top surface that is substantially continuous with an interior surface of the lumen of the hub.

5. The catheter system of claim 2, wherein the lumen of the hub defines a longitudinal axis, wherein the rear portion and leading portion of the spade define a width dimension that is transverse to the longitudinal axis, and wherein the width dimension of the rear portion is greater than the width dimension of the leading portion.

6. The catheter system of claim 2, wherein the spade defines a curved top surface.

7. The catheter system of claim 1, wherein the hub is made at least partially from a molded material, and wherein the molded material is overmolded on the slitter member to thereby fixedly couple the slitter member and the hub.

8. The catheter system of claim 1, wherein the lumen of the hub defines a longitudinal axis, and wherein a leading edge of the blade is disposed at a positive, acute angle with respect to the longitudinal axis.

9. The catheter system of claim 1, wherein the moveable member and the slitter member are generally on opposite sides of the lumen of the hub.

10. The catheter system of claim 1, wherein the moveable member is removably coupled to the hub via a break-away tab.

11. The catheter system of claim 10, wherein the moveable member includes a handle portion that extends generally transverse from a longitudinal axis of the lumen of the hub and that is configured to pull away from the hub in a direction generally transverse to a longitudinal axis of the lumen of the hub to break the break-away tab.

12. The catheter system of claim 10, further comprising a tube coupling member that couples the moveable member and the elongate tubular member, such that breaking the break-away tab enables pulling of the elongate tubular member toward the slitter member.

13. The catheter system of claim 10, wherein the break-away tab comprises an adhesive.

14. The catheter system of claim 10, wherein the break-away tab comprises molded material.

15. The catheter system of claim 1, wherein the lumen of the elongate tubular member is aligned with the lumen of the hub for passage of the instrument when the elongate tubular member is maintained in a fixed position relative to the hub.

16. The catheter system of claim 1, wherein the hub further comprises a guide loop to guide the elongate tubular member generally along a longitudinal axis when the elongate tubular member is moved relative to the hub.

17. A catheter system for positioning an instrument in a body, wherein the system comprises:
   an elongate tubular member extending from a proximal end to a distal end and defining a lumen therethrough;
   a hub comprising a proximal end and a distal end, wherein the hub defines a sealed passageway extending from the proximal end to the distal end along a longitudinal axis for passage of the instrument;
   a slitter member coupled to the hub configured to slit the elongate tubular member; and
   a movable member removably coupled to the hub and coupled to the elongate tubular member,
   wherein at least the movable member maintains the elongate tubular member in a fixed position relative to the hub prior to moving the movable member relative to the hub to advance the elongate tubular member such that the lumen of the elongate tubular member is aligned with the sealed passageway of the hub along the longitudinal axis for passage of the instrument from the sealed passageway to the lumen of the elongate tubular member when the instrument is being positioned in the body, and further wherein the elongate tubular member is removable from the hub by moving the movable member relative to the hub to advance the elongate tubular member to be sated toward the slitter member.

18. The catheter system of claim 17, wherein the system further comprises a tube coupling member fixedly coupling the moveable member to the elongate tubular member.

19. The catheter system of claim 17, wherein the catheter system further comprises a valve coupled to the hub and configured to inhibit backflow of bodily fluids from the sealed passageway.

20. The catheter system of claim 19, wherein the valve is further configured to selectively maintain the position of the instrument when the instrument is located in the sealed passageway.

21. The catheter system of claim 17, wherein the slitter member comprises:
 a blade configured to slit the elongate tubular member; and
 a spade coupled to the blade and at least partially locatable in the lumen of the elongate tubular member.

22. The catheter system of claim 21, wherein a leading edge of the blade is disposed at a positive, acute angle with respect to the longitudinal axis.

23. The catheter system of claim 17, wherein the hub further comprises a guide loop to guide the elongate tubular member generally along the longitudinal axis when the elongate tubular member is being removed from the hub.

24. A catheter system for positioning an instrument in a body, wherein the system comprises:
 an elongate tubular member extending from a proximal end to a distal end and defining a lumen therethrough;
 a hub comprising a proximal end and a distal end, wherein the hub defines a passageway extending from the proximal end to the distal end along a longitudinal axis, and further wherein the hub further comprises a guide loop;
 a slitter member coupled to the hub configured to slit the elongate tubular member; and
 a movable member removably coupled to the hub and coupled to the elongate tubular member,
 wherein at least the movable member maintains the elongate tubular member in a fixed position relative to the hub prior to moving the movable member relative to the hub to advance the elongate tubular member such that the lumen of the elongate tubular member is aligned with the passageway of the hub along the longitudinal axis, wherein the elongate tubular member is removable from the hub by moving the movable member relative to the hub to advance the elongate tubular member to be sated toward the slitter member, and further wherein the guide loop guides the elongate tubular member generally along the longitudinal axis when the elongate tubular member is being removed from the hub.

25. The catheter system of claim 24, wherein the passageway of the hub is sealed.

* * * * *

UNITED STATES PATENT AND TRADEMARK OFFICE
CERTIFICATE OF CORRECTION

PATENT NO. : 8,007,469 B2  
APPLICATION NO. : 12/182659  
DATED : August 30, 2011  
INVENTOR(S) : Niall Duffy Page 1 of 1

It is certified that error appears in the above-identified patent and that said Letters Patent is hereby corrected as shown below:

Column 11, Line 5, Claim 17, "...be seated toward...", should read --be slitted toward--

Column 12, Line 21, Claim 24, "...be sated toward...", should read --be slitted toward--

Signed and Sealed this
Third Day of January, 2012

David J. Kappos
*Director of the United States Patent and Trademark Office*